United States Patent
Strobel et al.

(10) Patent No.: US 6,902,573 B2
(45) Date of Patent: Jun. 7, 2005

(54) INSTRUMENTARIUM FOR IMPLANTING A TENDON REPLACEMENT

(75) Inventors: Michael Strobel, Straubing (DE); Michael Sauer, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 284 days.

(21) Appl. No.: 10/085,515

(22) Filed: Feb. 28, 2002

(65) Prior Publication Data

US 2002/0161439 A1 Oct. 31, 2002

Related U.S. Application Data

(63) Continuation of application No. PCT/EP00/08567, filed on Sep. 1, 2000.

(30) Foreign Application Priority Data

Sep. 1, 1999 (DE) .......................... 199 41 574

(51) Int. Cl.[7] .............................. A61B 17/04
(52) U.S. Cl. ...................... 606/232; 606/72; 606/103
(58) Field of Search .................... 606/232, 69, 72, 606/103, 233; D11/22; 24/90.1, 101 R, 102 A, 572

(56) References Cited

U.S. PATENT DOCUMENTS

| | | | |
|---|---|---|---|
| 3,135,032 A | * | 6/1964 | Althens ...................... 24/114.7 |
| 4,667,675 A | * | 5/1987 | Davis .......................... 606/233 |
| 5,306,301 A | | 4/1994 | Graf et al. ..................... 623/13 |
| 5,630,824 A | * | 5/1997 | Hart ............................ 606/139 |
| 6,006,404 A | * | 12/1999 | Sun ............................ 24/114.9 |
| 6,241,749 B1 | * | 6/2001 | Rayhanabad ................ 606/232 |

FOREIGN PATENT DOCUMENTS

| | | | |
|---|---|---|---|
| DE | 36 30 390 C2 | 8/1988 | |
| DE | 296 07 352 U1 | 9/1996 | |
| DE | 296 20 735 U1 | 3/1997 | |
| DE | 198 51 152 A1 | 5/2000 | |
| DE | 199 41 574 A1 | 3/2001 | |
| EP | 0 373 733 A1 | 6/1990 | |
| EP | 517151 | * 6/1992 | ........... A44B/1/32 |
| EP | 0 495 487 A2 | 7/1992 | |
| EP | 0 865 774 A1 | 9/1998 | |
| GB | 2 288 739 A | 11/1995 | |
| WO | WO 92/02196 | 2/1992 | |
| WO | WO 92/16167 | 10/1992 | |

* cited by examiner

Primary Examiner—Julian W. Woo
(74) Attorney, Agent, or Firm—St. Onge Steward Johnston & Reens LLC

(57) ABSTRACT

An instrumentarium for implanting a tendon replacement in a channel within a bone comprises a suture retention device. Said suture retention device has a plate-shaped body and a cylindrical pin projecting from said plate-shaped body. At least two openings extend through that plate-shaped body and said cylindrical pin for threading fixation threads of a tendon replacement therethrough. Said plate-shaped body having edges adapted for applying a tool for rotating said suture retention device (FIG. 13).

14 Claims, 8 Drawing Sheets

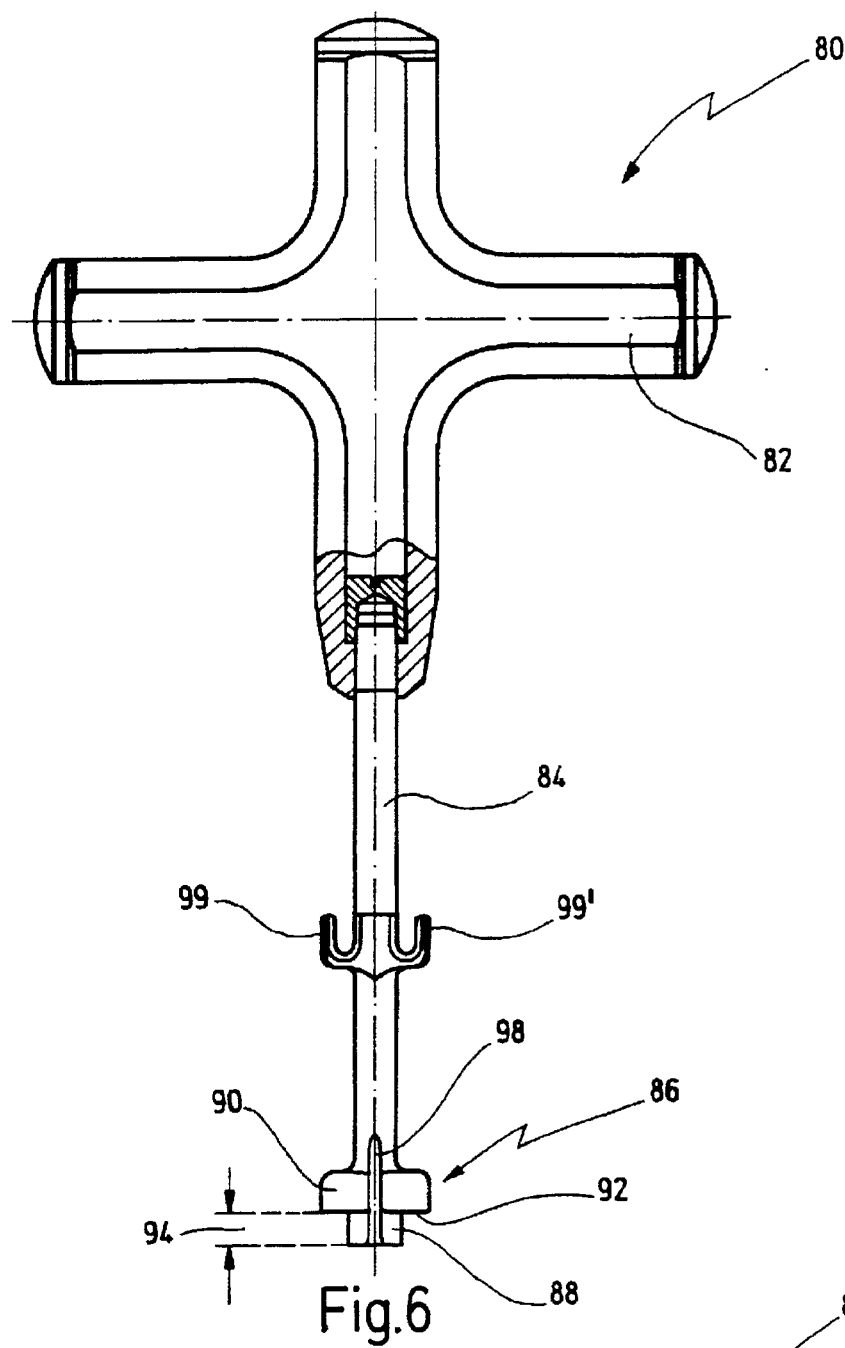
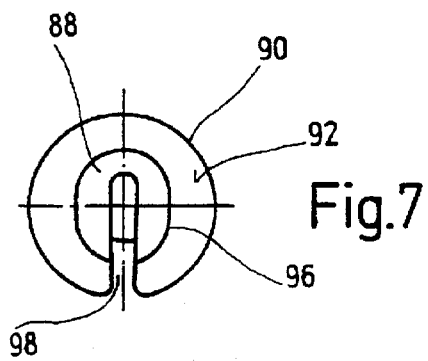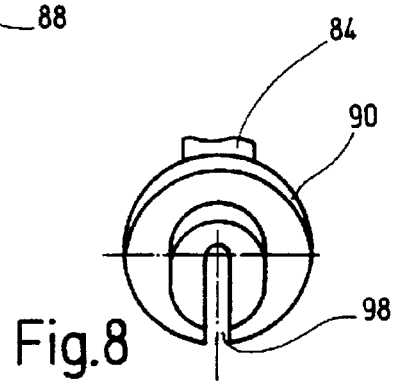

INSTRUMENTARIUM FOR IMPLANTING A TENDON REPLACEMENT

This application is a continuation of pending international application PCT/EP00/08567 filed on Sep. 1, 2000 which designates US and which claims priority of German patent application No. 199 41 574.9 filed on Sep. 1, 1999.

BACKGROUND OF THE INVENTION

The present invention relates to an instrumentarium for implanting a tendon replacement, especially a crucial ligament replacement in a knee-joint, having a button that can be placed against an outer opening of a bone channel in which the tendon replacement is arranged. The button comprises openings through which fixation threads of the tendon replacement can be threaded, and comprises further a central projection that extends into the outer opening of the bone channel when the button is applied against the latter.

An instrumentarium of this kind, and a corresponding operation technique in which that instrumentarium is employed, is known from the compendium "Michael Strobel; Arthroscopic Surgery", pp. 398 to 444 "Operation Technique", Springer-Verlag Berlin Heidelberg 1998. Such an instrumentarium has also been described in Applicant's German Patent Application No. 198 51 152.3, filed on Nov. 6, 1998.

For implanting a crucial ligament replacement in a knee-joint one produces a drilled channel, at a flexion angle of the knee-joint of approximately 60 to 90°, that extends through the distal end of the femur and also through the proximal end of the tibia. One then inserts into that drilled channel the tendon replacement, which is a natural tendon of the respective patient, for example the semitendinosus tendon. Fixation threads sewn to the ends of the tendines project from both ends of the drilled channel and serve to fix the tendon in place. The threads, which project from the outside of the femur, are usually fixed by means of a plate that rests against the outer opening of the drilled channel. The fixation threads projecting from the opposite end of the drilled channel, i.e. on the outside of the tibia, are fixed by means of what is known as a tibial button. This device for retaining the sutures is what is meant throughout this specification by the term "button".

The button has the general shape and size of a shirt button, which means that it comprises a circular main body having substantially the shape of a disk or the rim of a plate, with a central curved portion projecting on its one side and a corresponding depressed portion provided on its opposite side. The central portion is provided with openings through which the fixation threads can be threaded. A button of this kind is applied against the drilled channel so that its projection or curved portion comes to rest partially in the drilled channel. The fixation threads are threaded through the openings or holes, and are knotted in the manner illustrated by the respective sequence of operational steps shown in Strobel, loc. cit., p. 417. Regarded from the side, the contour of such a button is such that the projection rises, starting from its outer edge, along a smooth curvature to a rounded bulge from where it drops on the diametrically opposite side along a corresponding symmetric smooth S-shaped line.

It is a disadvantage of such a button that its central projection is supported in the opening of the drilled channel roughly along the latter's circumferential edge only so that it may get displaced, in particular get tilted, under load.

After the fixation threads threaded through the holes of the button have been knotted on the outside, the button so fixed can be turned a little in order to slightly increase the tension of the tendon. However, due to the fact that the button is supported in the outer opening of the drilled channel only along an outer circumferential line (see FIG. 14 of the present application), it is not guaranteed that the frictional engagement so produced will be sufficient to safely prevent the button from turning back and, thus, the tension of the tendon from being slackened.

EP-A-0 865 774 discloses an anchoring element intended for being connected to fixation threads of a tendon replacement, which is shaped as an oblong body that extends diametrically across the outer opening of the drilled channel and beyond both sides of the latter. The sections of the body that extend beyond the two sides of the outer opening are provided with nail-like elements that project toward the bone and that serve for being driven into the latter. The anchoring element is, therefore, nailed in place so that it extends transversely across the outer opening. In the area of the outer opening, the oblong body comprises a V-shaped recessed portion that projects into the drilled channel. The groove formed by the "V" receives the ends of the fixation threads which are knotted therein. It is a disadvantage of that arrangement that the anchoring element cannot be turned any more after the fixation threads have been knotted in the described element in order to tension the tendon, because the tendon is fixed against rotation by the nail-like pins that have been driven into the bone. In addition, the anchoring element is complex in shape and correspondingly expensive to produce.

Now, it is the object of the present invention to improve an instrumentarium for implantation of a tendon replacement so that the tendon replacement can be implanted easily, but yet correctly and safely seated.

SUMMARY OF THE INVENTION

This object is achieved by a button with a cylindrical pin being configured to come to snugly fit within a countersunk recess in a channel within the bone, an area of the plate-shaped body of said button surrounding said cylindrical pin being configured to come to rest to a bone surface surrounding said countersunk recess in said bone. Additionally, said plate-shaped body has edges adapted for applying a tool thereon for rotating said button with said tool.

These features provide the considerable advantage that the cylindrical pin sits snugly in the outer opening of the bone channel. The outer opening of the bone channel is provided for this purpose with a countersunk recess matching the pin-like neck. As a result of this close fit, the pin-like neck is in contact with the inner surface of the bone channel, over a relatively large surface area. A perfect fit is guaranteed which safely excludes any displacement or tilting of the button. The corresponding frictional fit also prevents any unwanted rotation of the button. Once the fixation thread has been knotted, this safe and perfect fit will be permanently maintained even under conditions of extreme movements and loading, for example during movement of a knee-joint.

The cylindrical pin is easy to produce and, correspondingly, the countersunk recess in the bone channel is likewise easy to produce and handling by the operator is simplified in this way. The fixation threads that project from the bone channel only have to be threaded through the openings of the button, which is then displaced along the stretched threads toward the opening of the bone channel, whereafter it can be inserted into the countersunk recess in exactly fitting fashion. The cylindrical pin permits the button to be turned after it has been inserted into the bone channel, in order either to correct its orientation or, later, after the fixation threads have been knotted, or to correct the tension of the tendon replacement by that rotation.

The area of the plate-shaped body surrounding the pin provides a further relatively large contact surface for the button resting against the outer bone surface.

The tension of the tendon, knotted to the button via the fixation threads, provides a frictional engagement that is sufficient to secure the button against rotation. Still, there remains the possibility, to overcome this frictional engagement and to rotate the button later, with the aid of a corresponding tool that will be described hereafter, for either increasing or reducing the tension of the tendon.

The edges of the button against which a tool can be applied for rotating the button provide the advantage that the edges provide easily visible orientation marks for the operator who wishes to apply such a tool, whereby handling is considerably simplified. The button, already connected via the threads to the tendon replacement can be rotated with the tool to enhance or to diminish the tension of the tendon replacement. The frictional engagement of the button with the bone areas via the outer surface of the cylindrical pin and via the area of the plate-shaped body surrounding the pin is strong enough to secure the button against rotation after removing the tool from the button.

According to a further embodiment of the invention, the plate-shaped body is provided with two opposite edges.

These design features facilitate handling of the button still further, especially when rotating the button, and further permit the forces acting upon the button during rotation to be distributed uniformly and symmetrically.

According to a further embodiment of the invention, the button is provided with a depression in the area of the openings on the side opposite the pin.

This feature provides the advantage that the knot of the fixation threads can be placed in that depression, and that the knots thereby come to lie in an oriented and fixed position.

According to a further embodiment of the invention, the depression verges into the openings via smooth curvatures.

This feature provides the advantage that the rubbing movements between the fixation threads and the button, that occur when the tendon expands or shortens, for example during movement of a knee-joint, cannot result in the threads being gradually worn through and, consequently, the connection getting detached.

According to a further embodiment, a setting device is provided comprising a distal setting tool by means of which the countersunk recess can be managed in the bone for the pin-like neck.

This feature provides the advantage that the setting device permits a countersunk recess to be produced in the area of the outer opening of the bone channel, into which the cylindrical pin of the button can be introduced in snugly fitting fashion.

According to a further embodiment of the invention the setting tool is provided, on its distal side, with a projecting pin the length of which corresponds substantially to the length of the cylindrical pin of the button.

This feature provides the advantage that the countersunk recess is worked down to exactly the depth that corresponds to the length of the cylindrical pin of the button.

As, usually, the drilled channel opens to the outside at an angle other than a right angle relative to the outer surface of the bone, it is thus possible to produce a countersunk recess whose longitudinal axis extends perpendicularly to the bone surface so that a button with a correspondingly simple rectangular geometry between plate-like body a projecting cylindrical pin can be used. This then necessarily results in a shoulder relative to the remaining bone channel at the outer end of the countersunk recess. This shoulder provides a further additional contact surface in the facial end face area of the pin-like neck.

According to a further embodiment of the invention, the setting pin of the tool comprises a limit stop on its proximal end.

This feature provides the advantage that handling of the tool for producing the countersunk recess is rendered especially easy for the operator. He only has to drive the tool into the bone until the stop comes to rest on the bone surfaces. This guarantees that the recess will not be made too deep so that, generally, the process can be carried out non-traumatically.

According to a further embodiment of the invention, the stop is configured as an annular flange.

This configuration is especially easy to produce, under constructional aspects, and results in a perfect fit of the countersunk recess, oriented right round and at the correct angle.

According to a further embodiment of the invention, the setting pin has an oval contour.

This feature provides the advantage that the oval pin can be driven into the bone non-traumatically. When the oval pin is rotated, the bone material is compacted, and one obtains a countersunk recess with a circular inner contour line.

According to a further embodiment of the invention, the setting tool of the setting device comprises a lateral longitudinal slot into which the fixation threads can be placed.

This feature provides the advantage that the tendon, together with the fixation threads, can first be placed in the drilled channel, and that the countersunk recess, into which the button is to be inserted, is produced thereafter. The fixation threads can then be placed in the lateral slot so that they will not be damaged, for example get jammed between the setting tool and the bone, when the setting tool is driven into the bone.

According to a further embodiment of the setting device, hooks for mounting the fixation threads are provided in a position remote from the setting tool.

This feature provides the further handling advantage that the fixation threads, having been bundled in the slot, can be mounted on the hooks and retained on the setting device so that they will not obstruct the operator's view or the operation field.

According to a further embodiment of the invention, it is provided that the setting device comprises a cross-shaped handle.

This configuration provides the possibility, on the one hand, to apply a hammer on the short upwardly projecting end of the cross in order to drive in the setting device, whereafter the operator can grip the cross-bars of the cross and rotate the latter, for example for managing a circular countersunk recess with a setting tool of oval cross-section.

According to a further embodiment of the invention, a knot holder is provided that comprises a handle and a distally projecting bar, whose distal end is provided with a notch intended to hold the fixation threads when they are knotted on the button.

This feature provides the advantage that the knot holder makes it possible to firmly hold not only the threads but simultaneously the button in contact with the bone channel when the knots are being looped and pulled tight.

According to a further embodiment of the invention, a tensiometer is provided whose distal end, that can be pulled out against the action of a spring, carries a hook that can be engaged in a loop of fixation threads formed on the button.

It is an aspect of this technique that an additional loop is fastened on the button. The loop can be used for engaging the tensiometer which can then be pulled to determine the force required for lifting off the button, from which a conclusion can then be drawn regarding the tensile force of the tendon. Depending on the result of that measurement it is then possible to either reduce or increase the tensile force by turning the button correspondingly. It is thus possible to adjust the optimum tensile force which is then permanently guaranteed due to the firm and immovable fit of the button.

According to a further embodiment of the invention, a button-turning tool is provided that can be applied upon the button and by means of which the button can be turned.

This feature provides the advantage that this special turning tool allows the button to be turned even at a later time, after it has been fitted and knotted using the fixation threads, in order either to correct its position or, for example, to correct the tension of the tendon based on a measurement performed using the tensiometer.

A further embodiment provides that the button-turning tool comprises working surfaces that can be applied against the edges of the button.

This feature provides the advantage that by matching the configuration of the edges of the button on the one hand and of the button-turning tool on the other hand, it is possible to turn the button in an especially easy and safe fashion, which especially facilitates handling by the operator and permits the button to be turned, without being impaired, even under high tensile forces produced by a highly tensioned tendon.

It is understood that the features recited above and those yet to be explained below can be used not only in the respective combination indicated, but also in other combinations or in isolation, without leaving the context of the present invention.

BRIEF DESCRIPTION OF THE DRAWINGS

Exemplary embodiments of the invention are shown in the drawings and are explained in more detail in the description which follows. In the drawings:

FIG. 6 shows a side view, sectioned in part, of a setting device for the button according to FIG. 2;

FIG. 7 shows a greatly enlarged view of the distal end face of the setting device according to FIG. 6;

FIG. 8 shows a perspective view corresponding to the view of FIG. 7;

DETAILED DESCRIPTION OF THE DRAWINGS

As will become apparent from the description of the Figures that follow, the instrumentarium according to the invention will be discussed hereafter in detail also by way of a description of the different steps of the method for implanting a tendon replacement, on which the present invention is based.

Figure 1:
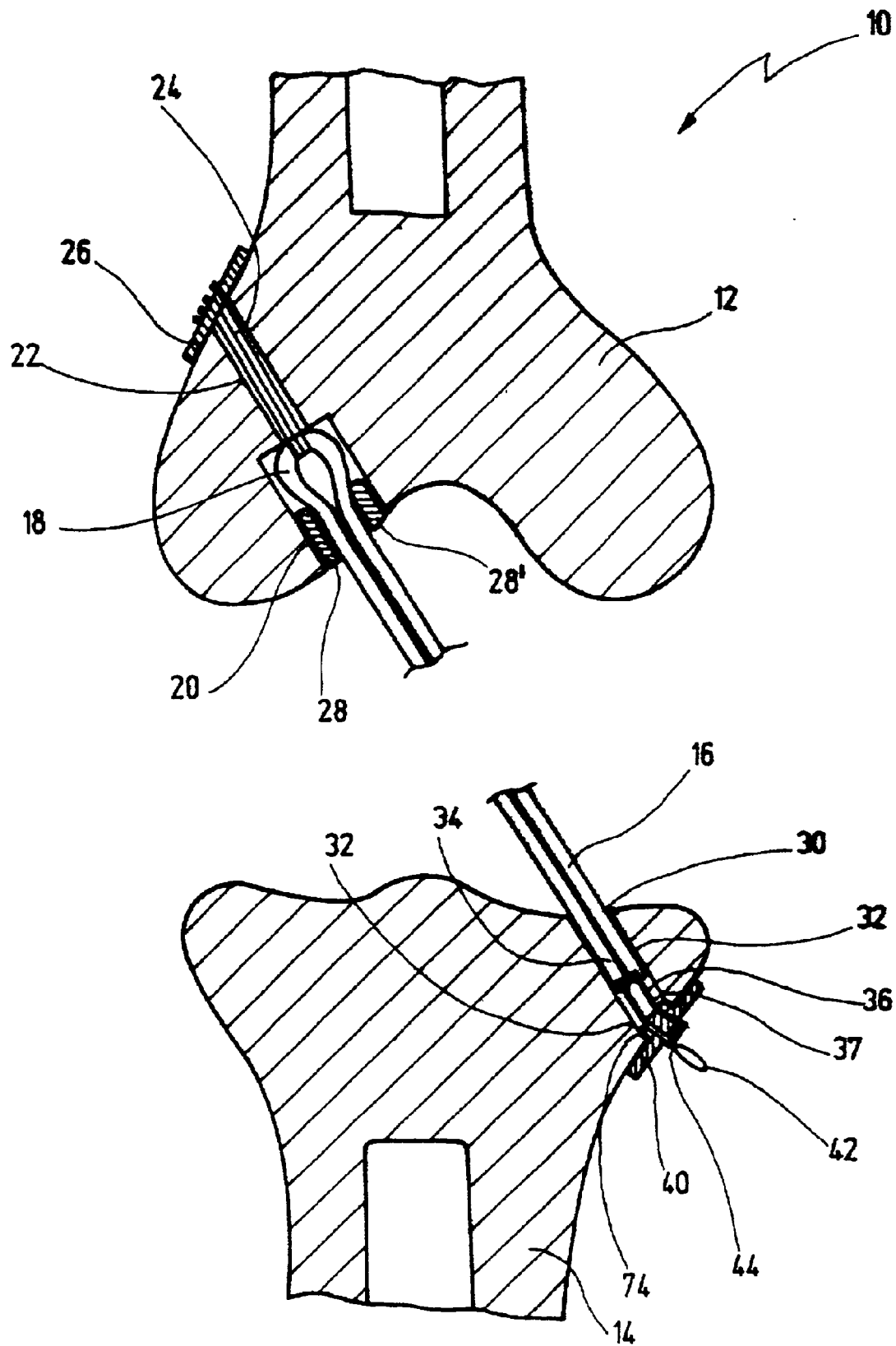
FIG. 1 shows a diagrammatic longitudinal section through a knee-joint with a substitute crucial ligament.
Figure 2:
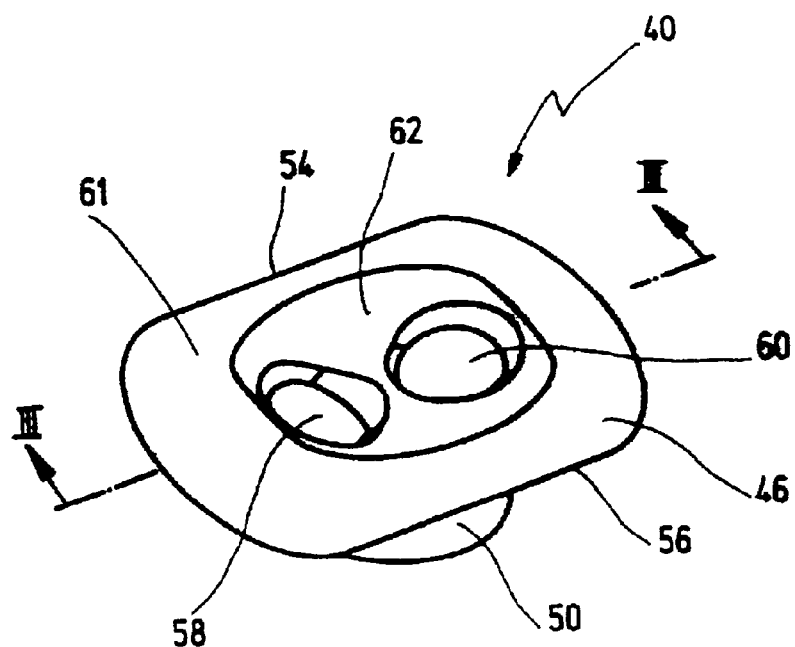
FIG. 2 shows a perspective top view of a button according to the invention.

Referring now to FIG. 1, a knee-joint, represented diagrammatically, is designated in its entirety by reference numeral 10.

The knee-joint 10 forms the connection between the distal end of the femur 12 and the proximal end of the tibia 14.

The two bones, which for the sake of clarity are shown at a spacing not true to scale, are connected by a tendon replacement 16, in the illustrated example by a substitute for the anterior crucial ligament.

The tendon of the tendon replacement 16 is prepared from a section of the patient's natural semitendinosus tendon. To this end, one takes a section of that tendon, cuts it to the desired shape and folds it over so that a double cord, forming a loop 18, is obtained.

The end of the tendon replacement 16, which comprises the loop 18, is slid into a blind bore 20 in the femur 12. The blind bore 20 is followed by a thinner drilled channel 22 that opens to the outer surface of the femur 20. The loop 18 is connected with a plurality of threads 24 that are guided through the drilled channel 22 and to the outside of the femur 12 where a plate 26 is fitted which is provided with openings, not shown in detail, through which the threads 24 are passed and knotted one with the other.

The tendon replacement 16 being broader in shape in the area of the loop 18, additional plugs 28 are introduced into the blind bore 20 in order to guarantee the immovable and firm seat of the tendon replacement 16 and to improve its growing processes. The end of the tendon replacement 16 opposite the end with the loop 18 is inserted into a passage bore 30 in the tibia 14. Each of the outer ends 34 of the tendon replacement 16 is sewn to fixation threads; in FIG. 1, only two fixation threads 36 and 37 are shown as being connected with one tendon cord. The four fixation threads project from the opening 33 of the bone channel 32 formed by the bore 30 and are connected at this point with a button 40 by a plurality of knots 44. There is further provided a loop 42 that will be removed later, after adjustment of the tendon replacement.

Referring to the following Figures, there will now be described and discussed the constructional design of the button and the way in which it is brought into its proper position.

The button 40, shown in detail in FIGS. 2 to 5, comprises a substantially plate-shaped body 46 with a pin-like neck 50 projecting from that side 48 that faces the outside of the tibia 14 during implantation.

The pin-like neck 50 is shaped as a cylindrical pin 52.

The body 46 comprises two opposite longitudinal edges 54 and 56, extending in parallel one to the other, whose outer ends are connected via smoothly rounded portions so that, viewed from above, a roughly rectangular contour with opposite straight edges 54 and 56 is seen.

Figure 3:
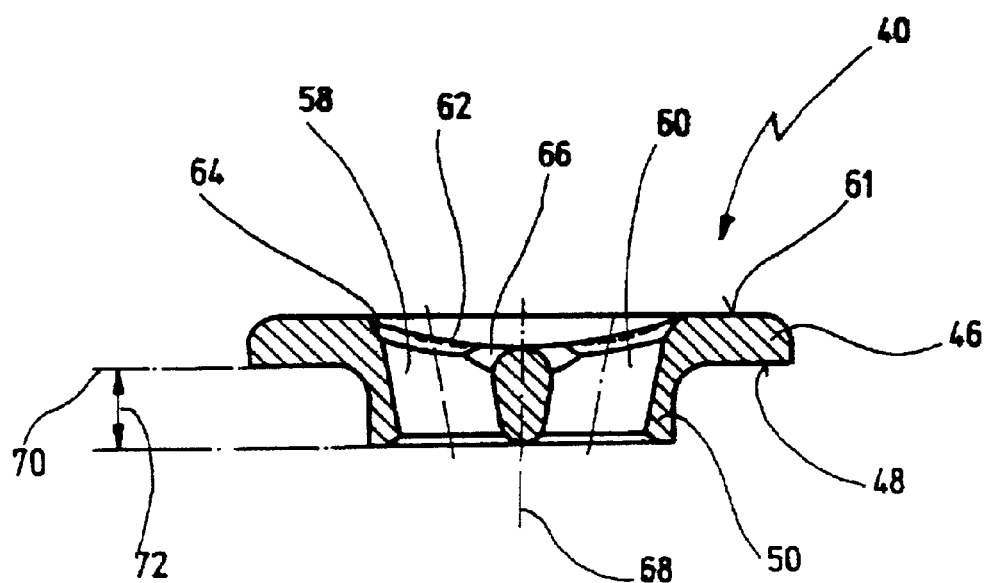
FIG. 3 shows a cross-section taken along line III—III in FIG. 2.
Figure 4:
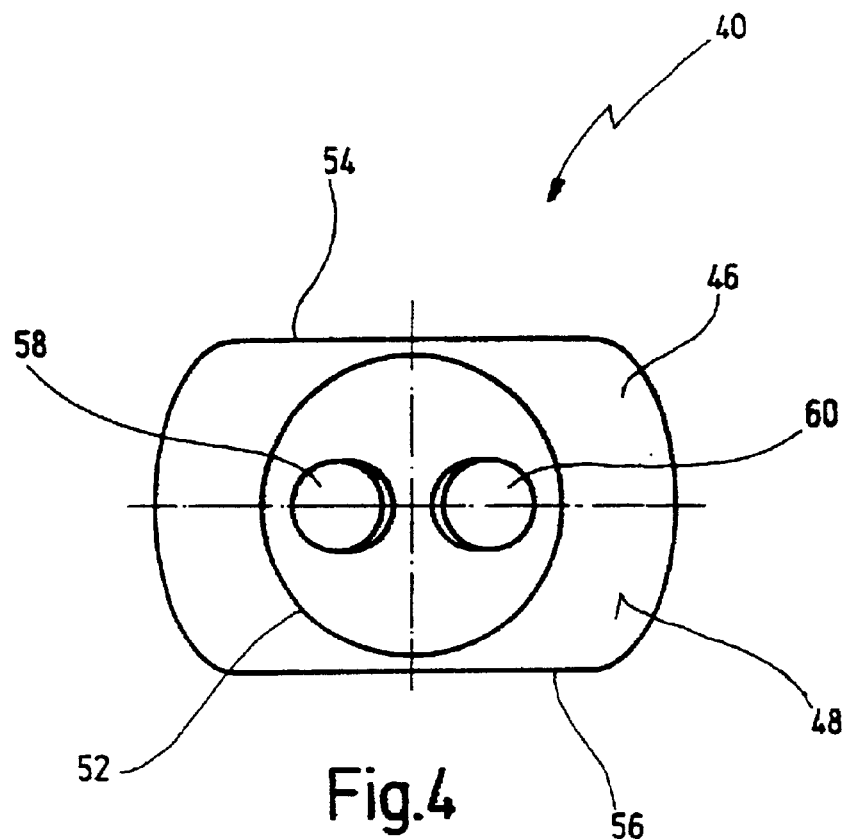
FIG. 4 shows a view of the button from below, i.e. from that side of the bone against which the button is to be applied.
Figure 5:
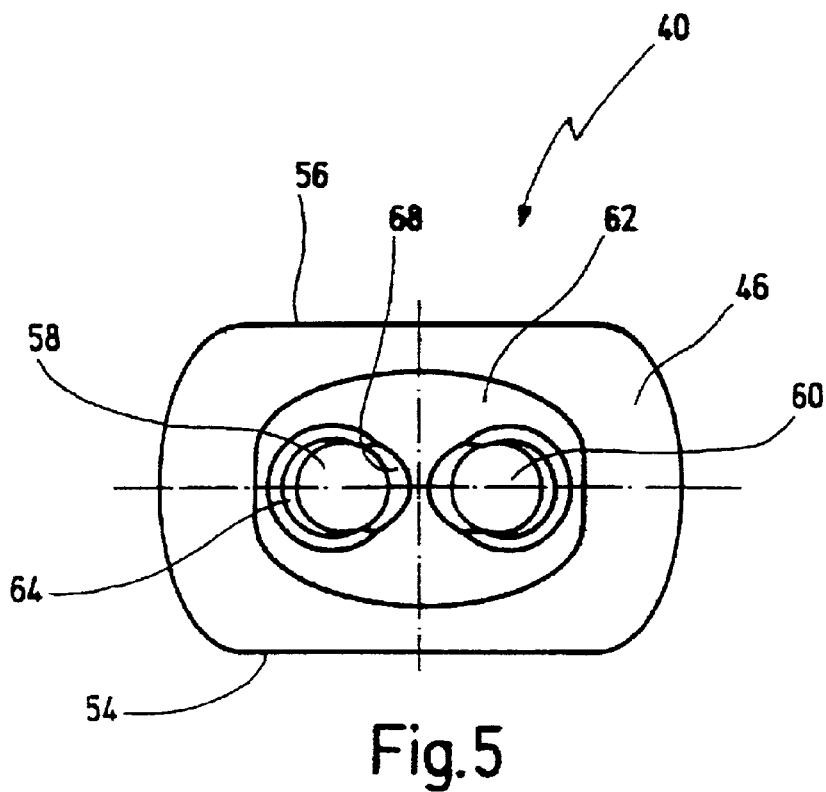
FIG. 5 shows a top view of the button illustrated in FIG. 2.

Two openings 58 and 60 provided in the central portion extend through the body 46 and through the cylindrical pin 52, as can be seen best in the sectional representation of FIG. 3. The body 46 is provided with a depression 62 on the side 61 opposite the pin 52. The depression 62 verges into the opening 58 via smooth curvatures 64 and 66, respectively; the same applies by analogy to the transition to the opening 60. As can be seen in particular in the sectional view of FIG. 3, the longitudinal axis or the pin axis 68 extends substantially at a right angle relative to a plane 70 that extends along the lower flat level side 48 of the body 46.

The neck 50 projecting from the body 46 of the button 40 is intended to be inserted into a countersunk recess 74 (see FIGS. 1 and 13) in the area of the outer opening 33 of the drilled channel. The length 72 of the neck 50 corresponds to the depth of the countersunk recess 74, the clear diameter of the countersunk recess 74 corresponds to the outer diameter of the cylindrical pin 52 so that the latter can be received snugly in the countersunk recess 74.

As has been mentioned before, the bone channel 32 through the tibia 14 is produced by drilling using a drilling tool. For producing the countersunk recess 74 adapted to the contour of the pin 52 of the button 40 a setting device 80 is provided, as shown in FIGS. 6 to 8.

The setting device 80 comprises for this purpose a substantially cross-shaped handle 82 with a distally projecting rod 84 carrying a setting tool 86 on its extreme distal end.

The setting tool 86 comprises a pin 88 whose proximal end is surrounded by an annular flange 90 the distal annular surface of which serves as stop 92.

The pin 88 has a length 94 that corresponds to the length 72 of the pin 52 of the button 40.

From the end view of FIGS. 7 and 8, respectively, it can be seen that the pin 88 has an oval contour 96. A slot 98, extending in the lengthwise direction of the rod 84, is provided laterally in the area of the setting tool 86. As can be seen best in FIG. 7, the slot 98 extends radially beyond the annular flange 90 up to the area of the pin 88.

At a certain distance from the tool 86 in proximal direction, the rod 84 is further provided with two hooks 99, 99'.

The countersunk recess 74, into which the pin 52 of the button 40 is to be inserted, is produced with the aid of the setting device 80 as follows. The four fixation threads 36, 37, 38 and 39 projecting from the bone channel 32 on the side of the tibia 14 are bundled, the setting device 80 is applied, the bundled fixation threads are placed laterally into the slot and are engaged in the hooks 99, 99', respectively. The setting device 80, or rather its setting tool 36, is applied to the oval opening 33, and the setting device 80 is driven in, if necessary, using a hammer for example, until the stop 92 comes to rest against the outside of the tibia 14. The orientation of the longitudinal axis of the rod 84 of the setting device 80 is such that it extends at a substantially right angle to the bone surface surrounding the opening 33 of the bone channel 32. Once the setting device 18 has been driven in the required length, the device is rotated so that the countersunk recess 74 is produced in the bone by the turning motion of the tool 86.

Figure 13:
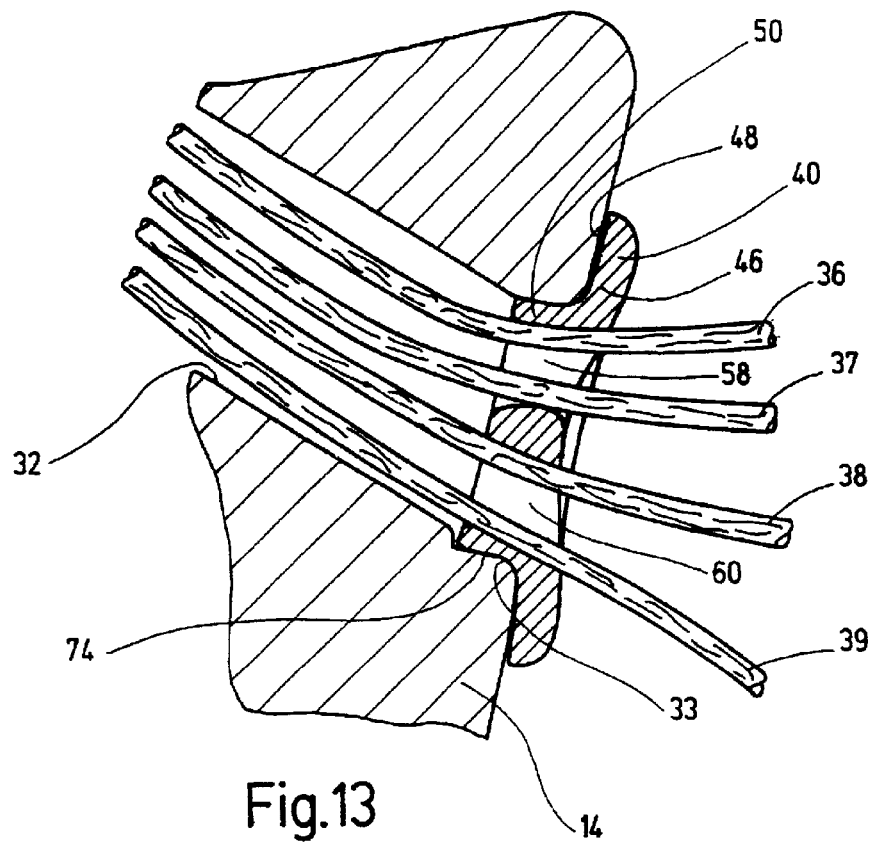
FIG. 13 shows a greatly enlarged view of a button applied to the outer opening of the bone channel, with four fixation threads threaded trough its openings.

After the countersunk recess 74 has been properly formed, the setting device 80 is withdrawn, and a button 40 is threaded onto the four fixation threads 36 to 39, as illustrated in FIG. 13. As can be seen in that Figure, two fixation threads 36 and 37 have been threaded through the opening 58, two other fixation threads 38 and 39 through the opening 60.

The button 40 has its pin 52 seated snugly in the countersunk recess 74 in the area of the opening 33 of the bone channel 32. At the same time, the body 46 of the button has its bottom surface 48 surrounding the pin 52 resting flat against the outside of that area of the tibia 14 which surrounds the opening 33. The sectional view of FIG. 13 demonstrates in an especially impressive way that the button 40 is seated snugly and in an exactly oriented and, above all, stable way over a large surface area both in the area of the bottom 46 and in the area of the pin-like neck 50.

Figure 14:
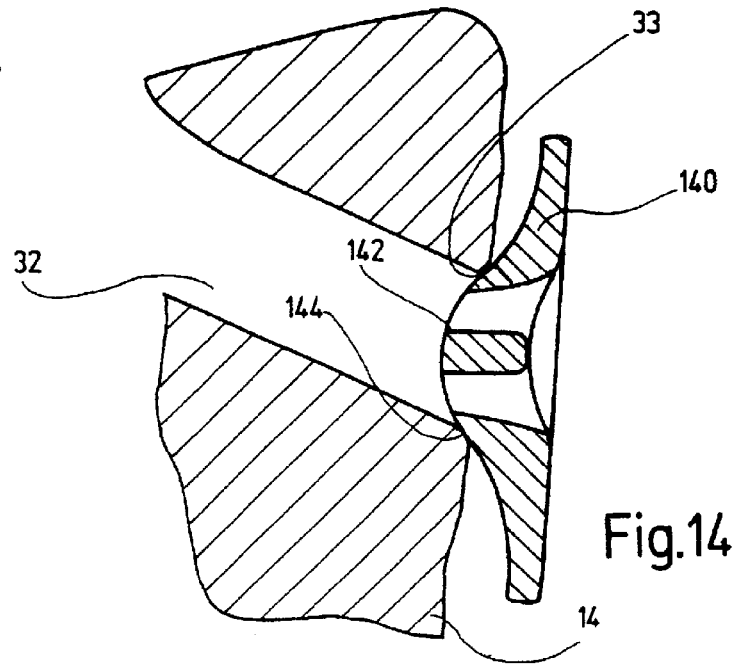
FIG. 14 shows a representation, similar to that of FIG. 13, of a button applied to the outer opening of the bone channel, according to the prior art as discussed at the outset.

This exactly is a problem with the button 140 of the prior art as described at the outset and as shown in FIG. 14. A button 140 of that kind, known from the prior art, comprises a hump-like projection 142 that extends into the opening 33 a smaller or greater amount. In addition, it can be seen that such a button 140, once applied, rests on the bone substantially along a line 144 that corresponds to the outer edge of the bone channel 32. This allows the bone 140 to be tilted or canted.

Figure 9:
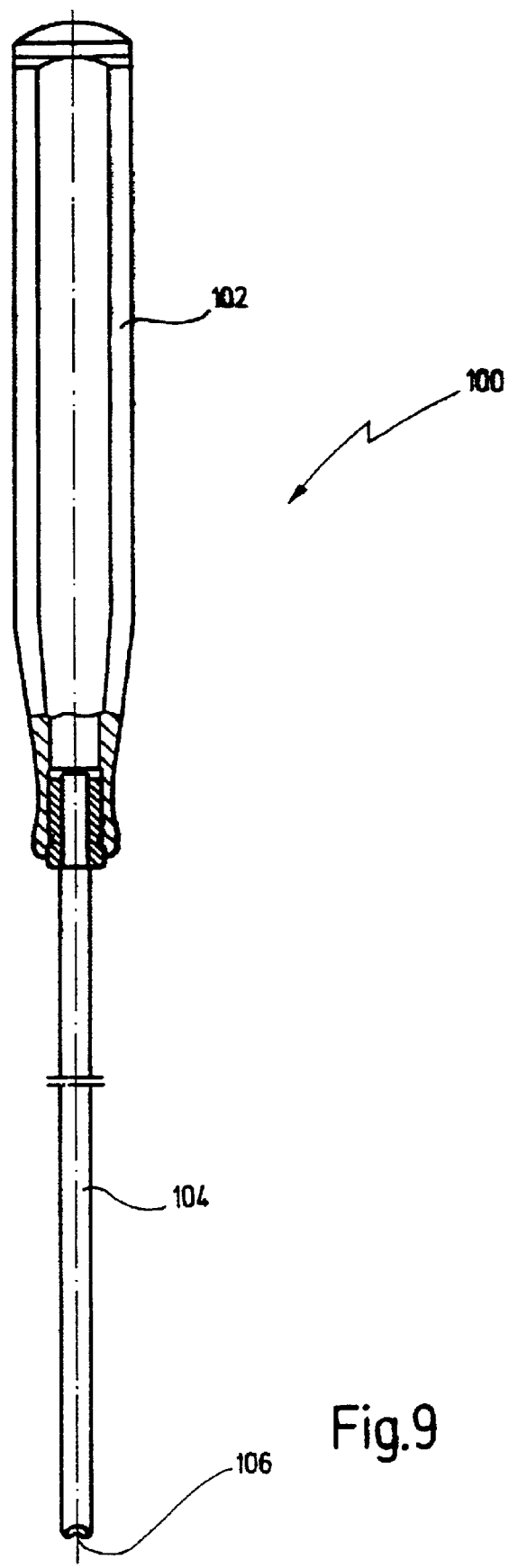
FIG. 9 shows a side view of a knot holder that serves to facilitate the knotting operation on the button according to FIG. 2.

Reverting to the representation of FIG. 13, the fixation threads are now knotted one with the other, and the tendon replacement 16 is tensioned. In order to facilitate the knotting process, and for holding both the button 40 and a fixation thread threaded through it, the knot holder 100 shown in FIG. 9 is provided. The knot holder 100 comprises a handle 102 with a rod 104 projecting distally therefrom, whose outer distal end is provided with a notch 106.

The notch 106 serves to apply the knot holder to either a fixation thread or a knot already formed, in order to permit that thread or knot to be knotted with other threads. After completion of that operation, a structure as shown in FIG. 1 is obtained. Using the additional loop 42 it is now possible to check the tension of the tendon replacement 16.

Figure 10:
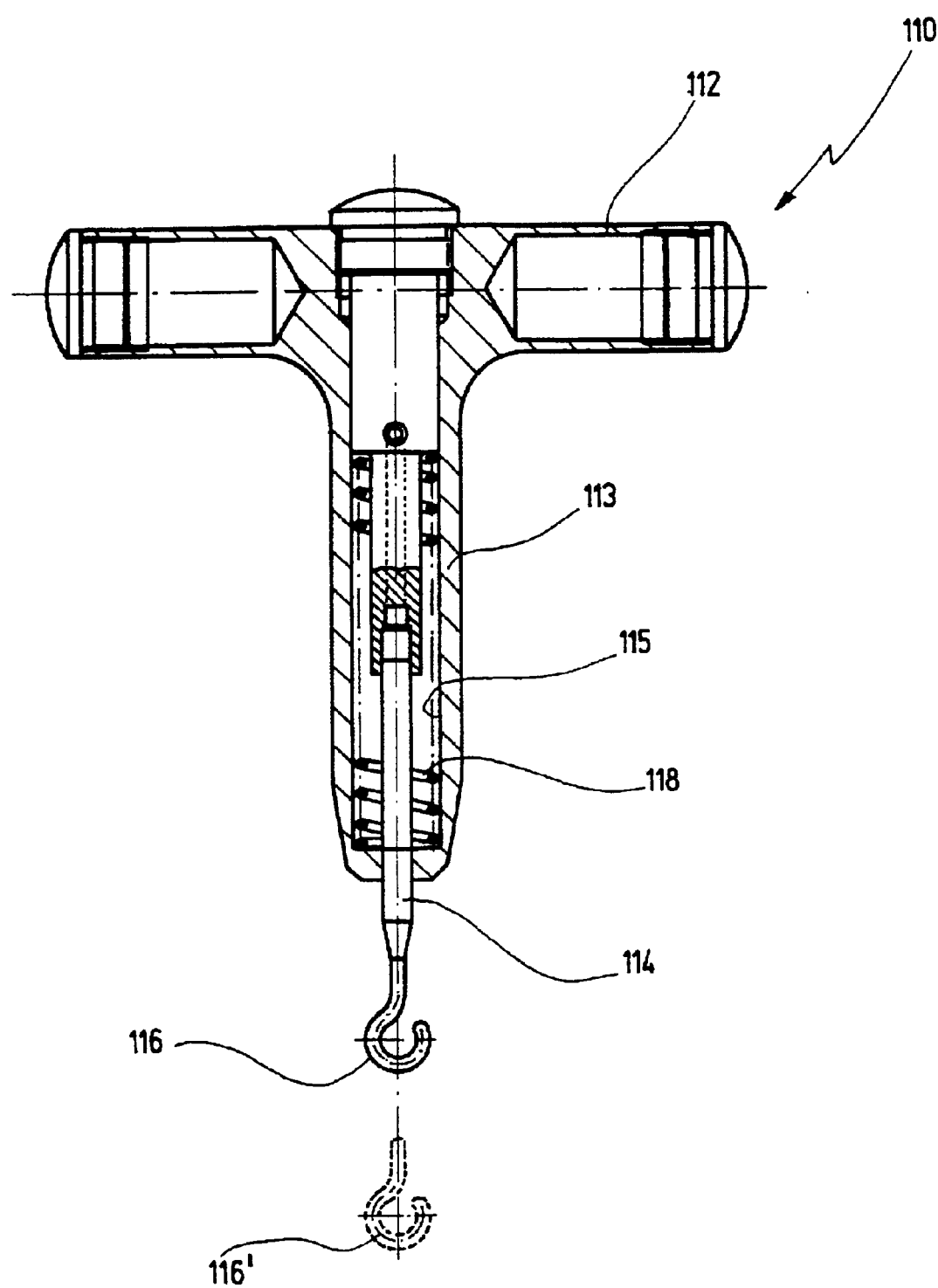
FIG. 10 shows a tensiometer for measuring the tension at which the button rests against the bone after it has been knotted using the fixation threads.

This is achieved with the aid of a tensiometer 110 as shown in FIG. 10.

The tensiometer 110 comprises a handle 112 with a hollow shaft 113 projecting distally therefrom.

The hollow shaft 113 accommodates a rod 114, the outer distal end of which is provided with a hook 116. The rod 114 can be withdrawn from the shaft 113 against the action of a spring 118. Suitable marks, not shown in the drawing, permit a conclusion to be drawn regarding the force required to pull the rod 114 a certain length out of the shaft 113. For checking the tension of the tendon replacement 16, one engages the hook 116 of the tensiometer 110 in the loop 42 and pulls until the button 40 is about to be lifted off. The corresponding pulled-out position of the hook 116 is illustrated in broken lines in FIG. 10.

Figure 11:
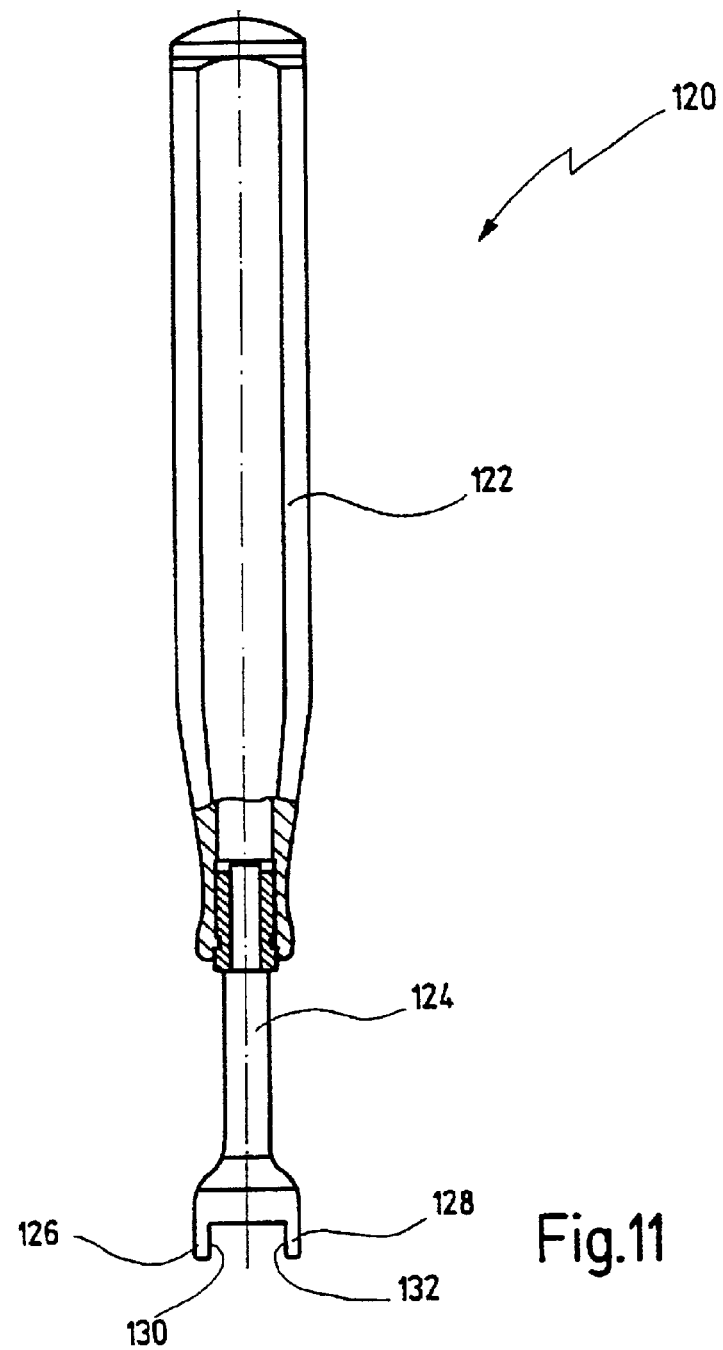
FIG. 11 shows a button-turning tool for turning the button illustrated in FIG. 2.
Figure 12:
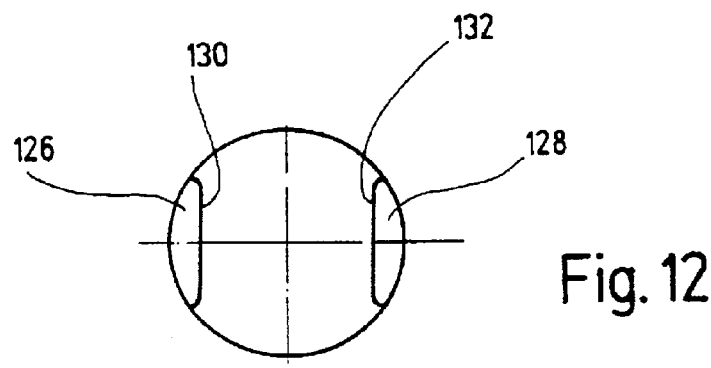
FIG. 12 shows a greatly enlarged view of the distal end face of the button-turning tool of FIG. 11.

If the tension of the tendon replacement 16 is correct, the button 40 can be left in its position. If the tension is still insufficient, for example, the button 40 may be turned so as to drill and tension the fixation threads and the tendon replacement, respectively. This operation is effected using the button-turning tool 120 illustrated in FIGS. 11 and 12.

The button-turning tool 120 comprises a handle 122 with a proximally projecting rod 124. The distal end of the rod 124 is provided with two jaws 126 and 128, whose inner diametrically opposite straight working surfaces 130 and 132 are suitably designed and spaced one from the other a suitable distance so that they can be applied from the outside upon the corresponding edges 54 and 56 (see especially FIG.

2) of the button 40. By turning the button-turning tool 120 so applied, the button 40 is then rotated whereby the tendon replacement 16 is tensioned.

The large-area fit of the button 40 that can be seen especially well in FIG. 13 guarantees sufficient frictional engagement to ensure that a button 40, having been turned using the button-turning tool 120, will remain in its position and will not be turned back by the reset force produced by the twist. This also demonstrates the advantage over the design of the before-mentioned EP-A-0 865 774 which uses nail-like anchoring means and which, therefore, does not allow the tendon replacement to be turned and tensioned later.

What is claimed is:

1. Instrumentarium for implanting a tendon replacement in a channel in a bone comprising
    a suture retention device,
    said suture retention device having a plate-shaped body with first and second sides,
    a cylindrical pin projecting from the first side of said plate-shaped body;
    a recess in the second side of said plate-shaded body for accommodating ends of fixation threads of a tendon replacement; and
    at least two openings extending through said plate-shaped body and said cylindrical pin for threading of the fixation threads of the tendon replacement therethrough, wherein said recess verges into each opening via a plurality of curved surfaces, and
    wherein said cylindrical pin being configured to come to snugly fit within a countersunk recess in a channel within a bone, an area of said plate-shaped body surrounding said cylindrical pin being configured to come to rest to a bone surface surrounding said countersunk recess in said bone, and wherein said plate-shaped body having edges adapted for applying a turning tool thereon for turning said device with said tool.

2. The instrumentarium of claim 1, wherein said plate-shaped body is provided with two opposite edges.

3. The instrumentarium of claim 1, wherein said cylindrical pin projects from a planar side of said plate-shaped body of said suture retention device.

4. Instrumentarium for implanting a tendon replacement in a channel in a bone comprising
    a suture retention device,
    said suture retention device having a plate-shaped body,
    a cylindrical pin projecting from said plate-shaped body and
    at least two openings extending through said plate-shaped body and said cylindrical pin for threading fixation threads of a tendon replacement therethrough wherein said cylindrical pin being configured to come to snugly fit within a countersunk recess in a channel within a bone, an area of said elate-shaped body surrounding said cylindrical pin being configured to come to rest to a bone surface surrounding said countersunk recess in said bone, and wherein said plate-shaped body having edges adapted for applying a turning tool thereon for turning said device the said tool; and
    a setting device comprising a distal setting tool by means of which setting tool a countersunk recess can be managed in said bone corresponding to said cylindrical pin projecting from said plate-shaped body.

5. The instrumentarium of claim 4, wherein said setting tool is provided with a projecting pin, a length of which pin corresponds substantially to a length of the cylindrical pin projecting from said plate-shaped body of said suture retention device.

6. The instrumentarium of claim 5, wherein said projecting pin comprises a limit stop on a proximal end thereof.

7. The instrumentarium of claim 6, wherein said stop is configured as an annular flange.

8. The instrumentarium of claim 7, wherein said projecting pin has an oval contour.

9. The instrumentarium of claim 4, wherein a lateral longitudinal slot is provided in said setting device into which slot fixation threads for fixing said tendon replacement can be placed.

10. The instrumentarium of claim 9, wherein hooks for mounting said fixation threads are provided in a position remote from said setting tool of said setting device.

11. The instrumentarium of claim 10, wherein said setting device comprising a cross-shaped handle.

12. Instrumentarium for implanting a tendon replacement in a channel in a bone comprising
    a suture retention device,
    said suture retention device having a plate-shaped body,
    a cylindrical pin projecting from said plate-shaped body and
    at least two openings extending through said plate-shaped body and said cylindrical pin for threading fixation threads of a tendon replacement therethrough wherein said cylindrical pin being configured to come to snugly fit within a countersunk recess in a channel within a bone, an area of said plate-shaped body surrounding said cylindrical pin being configured to come to rest to a bone surface surrounding said countersunk recess in said bone, and wherein said plate-shaped body having edges adapted for applying a turning tool thereon for turning said device with said tool; and
    a knot holder comprising a handle and a bar projecting distally there from, whose distal end is provided with a notch intended to hold fixation threads when they are being knotted on said suture retention device.

13. Instrumentarium for implanting a tendon replacement in a channel in a bone comprising
    a suture retention device,
    said suture retention device having a plate-shaped body,
    a cylindrical pin projecting from said plate-shaped body and
    at least two openings extending through said plate-shaped body and said cylindrical pin for threading fixation threads of a tendon replacement therethrough wherein said cylindrical pin being configured to come to snugly fit within a countersunk recess in a channel within a bone, an area of said plate-shaped body surrounding said cylindrical pin being configured to come to rest to a bone surface surrounding said countersunk recess in said bone, and wherein said plate-shaped body having edges adapted for applying a turning tool thereon for turning said device with said tool; and
    a tensiometer, whose distal end can be pulled out against an action of a spring, said distal end carrying a hook that can be engaged into a loop of fixation threads formed on said suture retention device.

14. Instrumentarium for implanting a tendon replacement in a channel in a bone comprising
    a suture retention device,
    said suture retention device having a plate-shaped body,
    a cylindrical pin projecting from said plate-shaped body and at least two openings extending through said plate-shaped body and said cylindrical pin for threading fixation threads of a tendon replacement therethrough wherein said cylindrical pin being configured to come to snugly fit within a countersunk recess in a channel within a bone, an area of said plate-shaped body surrounding said cylindrical pin being configured to come to rest to a bone surface surrounding said countersunk recess in said bone, and wherein said plate-shaped body having edges adapted for applying a turning tool thereon for turning said device with said tool; and a button turning tool that can be applied upon said edges on said device for rotating said suture retention device.

* * * * *